United States Patent
Ehring

(10) Patent No.: US 10,094,770 B2
(45) Date of Patent: *Oct. 9, 2018

(54) POLYMERIC DEVICE SUITABLE FOR ULTRAVIOLET DETECTION

(71) Applicant: GE HEALTHCARE BIO-SCIENCES AB, Uppsala (SE)

(72) Inventor: Hanno Ehring, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 277 days.

This patent is subject to a terminal disclaimer.

(21) Appl. No.: 15/200,722

(22) Filed: Jul. 1, 2016

(65) Prior Publication Data

US 2016/0313240 A1    Oct. 27, 2016

Related U.S. Application Data

(63) Continuation of application No. 13/891,340, filed on May 10, 2013, now Pat. No. 9,404,862, which is a continuation of application No. 12/032,197, filed on Feb. 15, 2008.

(30) Foreign Application Priority Data

Feb. 20, 2007  (GB) .................................. 0703175.0

(51) Int. Cl.
*G01N 21/05* (2006.01)
*G01N 21/33* (2006.01)
*G01N 21/59* (2006.01)
*A61L 2/08* (2006.01)
(Continued)

(52) U.S. Cl.
CPC ............... *G01N 21/33* (2013.01); *A61L 2/08* (2013.01); *G01N 21/05* (2013.01); *G01N 21/59* (2013.01); *G01N 30/74* (2013.01); *A61L 2202/11* (2013.01); *G01N 2021/0346* (2013.01); *G01N 2201/062* (2013.01)

(58) Field of Classification Search
CPC ....................................................... G01N 21/05
USPC .............................. 356/246; 250/431, 461.2
See application file for complete search history.

(56) References Cited

U.S. PATENT DOCUMENTS

| 3,401,591 A | 9/1968 | Anthon |
| 5,194,586 A | 3/1993 | Maeda et al. |
| 5,885,470 A | 3/1999 | Parce et al. |

(Continued)

FOREIGN PATENT DOCUMENTS

| EP | 0423649 | 4/1991 |
| EP | 1 557 658 | 7/2005 |

(Continued)

OTHER PUBLICATIONS

The Stovall Flow Cell; <http://www.slscience.com/ftowcell.hl ml>.
(Continued)

*Primary Examiner* — Tri Ton
*Assistant Examiner* — Rebecca C Bryant
(74) *Attorney, Agent, or Firm* — Wood IP LLC

(57) ABSTRACT

The present invention relates to a flow cell (10) comprising a fluid inlet (16) and a fluid outlet (18) separated by a sample flow-through chamber (12) comprising at least one UV-transparent window (22'), wherein the at least one UV-transparent window (22') is made of a polymer material and has been subjected to Gamma radiation sterilisation. In one aspect, the flow cell is combustible.

20 Claims, 3 Drawing Sheets

(51) Int. Cl.
*G01N 30/74* (2006.01)
*G01N 21/03* (2006.01)

(56) References Cited

U.S. PATENT DOCUMENTS

| | | |
|---|---|---|
| 2003/0036101 A1 | 2/2003 | Schrattenholz |
| 2004/0120848 A1 | 6/2004 | Teodorczyk |
| 2004/0142484 A1 | 7/2004 | Berlin et al. |
| 2006/0182664 A1 | 8/2006 | Peck et al. |
| 2006/0221330 A1 | 10/2006 | Waldo |

FOREIGN PATENT DOCUMENTS

| | | |
|---|---|---|
| JP | 09-220214 | 8/1997 |
| JP | 10-038795 | 2/1998 |
| JP | 2000-214083 | 8/2000 |
| JP | 2005008685 | 6/2003 |
| JP | 2004-037409 | 2/2004 |
| JP | 2004-354285 | 12/2004 |
| WO | WO 2001/058432 | 8/2001 |
| WO | WO 02/29397 | 4/2002 |
| WO | WO 02175284 | 9/2002 |

OTHER PUBLICATIONS

Sinco, Patrick, "Inside a gamma sterilizer," Isotopes & Radiation, Nuclear News May 1999, pp. 92-96.
Search Report from India in corresponding Indian application No. 3817/DELNP/2009.

POLYMERIC DEVICE SUITABLE FOR ULTRAVIOLET DETECTION

CROSS-REFERENCE TO RELATED APPLICATIONS

This application is a continuation of U.S. patent application Ser. No. 13/891,340, filed May 10, 2013, which is a continuation of Ser. No. 12/032,197, filed Feb. 15, 2008, which claims priority to application number 0703175.0 in United Kingdom, the entire contents of which are hereby incorporated herein by reference.

FIELD OF THE INVENTION

The present invention relates to a polymer based device and its manufacturing methods. The device is suitable for the ultra violet detection of bio molecules such as proteins and nucleic acids in a liquid media.

BACKGROUND OF THE INVENTION

There is a large volume of literature related to development of devices suitable for ultraviolet (UV) detection, typically used as detectors in systems for the filtration, or chromatographic or electrophoretic separation of bio molecules.

Traditionally, quartz has been the preferred material for use in devices for UV detection because it is UV transparent. However, quartz suffers from a number of disadvantages: it is more expensive than polymeric materials and the manufacturing process for quartz devices is relatively complicated and expensive. Accordingly, quartz devices are not found to be suitable for disposable systems. There is a significant interest in disposable systems, in particular for use in strictly regulated processes, for example separation or purification of chemicals, bio molecules or other components for use in pharmaceutical applications. Materials used in such systems must fulfil the requirements for United States Pharmacopeia (USP) class VI to guarantee that they do not release harmful substances during use. While this criteria has less relevance for systems to be used for analytical purposes, it is a vital criteria for systems intended for preparative purposes. Such systems for preparative purposes should also provide a sterilised environment in order to meet the strict hygiene requirements for such applications. Accordingly, it should be possible to sterilise the system. Sterilisation is herein construed to mean reduction of microbial population.

Equipment can be sterilised by the use of several methods, for example by the use of 100% ethylene oxide gas. However, this method has a number of disadvantages. First, after sterilisation the equipment has to be transferred to an aeration cell, where it remains until the gas has dispersed and the equipment is safe to handle. Further, the gas may not penetrate to all cavities within the equipment to be sterilised, and seals may be stressed. Additionally, gas permeable packaging materials may have to be used, to allow gas to flow through.

Gamma irradiation is another method used to sterilise equipment. Gamma irradiation sterilisation is herein construed to mean reduction of microbial population by the use of gamma irradiation. Typically, a radiation dose of 25 kGy is used for this purpose and the radiation source is typically $^{60}$Co, but $^{137}$Cs can also be used. The radiation dose should be at least 15 kGy. For radiation doses less than 15 kGy, for example 10 kGy, the regulatory authorities require a list of all the bacteria present in the system to be sterilised, as well as proof that all the listed bacteria have been killed. Therefore it is preferable to use a radiation dose higher than 15 kGy. Acceptance test criteria for sterility following gamma irradiation are provided in the test USP <85>, and include results for microbial burden (CFU/100 ml) and endotoxin levels (EU/ml) in flow through. The use of gamma irradiation overcomes the disadvantages mentioned above for ethylene oxide sterilisation. Packaging of equipment remains intact during gamma irradiation and seals are not stressed. The gamma radiation penetrates deep into most materials, and eliminates the need for gas permeable packaging materials. Following gamma irradiation, the equipment can be used immediately as it leaves no harmful residue or contaminants.

The sterilisation of equipment by gamma irradiation for use in devices for non-UV detection is well known in the art. Thus, for example, continuous culture chambers or flow cells for use in the on-line microscopic study of biofilm growth are available (e.g. Stovall Life Sciences, Inc. website. As visible light is used in such applications, as opposed to UV detection, many materials can be used which still transmit in the visible range even after gamma irradiation.

The use of polymeric materials in devices for UV detection is described in WO02/29397. WO02/29397 discloses the use of cycloolefin copolymer or an amorphous fluoropolymer preferably a fluoropolymer known as TEFLON AF®) in a device for UV detection. It also discloses the use of TOPAS® (a copolymer of ethylene and norbornene) which is said to transmit UV at>50% efficiency above 250 nm. However, most cycloolefin copolymers (polymers made from norbornene monomers) are not USP classified. Furthermore, many cycloolefin copolymers will block UV radiation after gamma irradiation treatment. In fact, most polymers tend to block UV radiation after having been subjected to gamma irradiation treatment. TEFLON AF® amorphous fluoropolymer is very expensive as raw material, which makes it economically unsuitable for a disposable device.

U.S. Pat. No. 5,885,470 discloses polymer devices made of polydimethylsiloxane (PDMS), polymethyl methacrylate (PMMA), polyurethane, polysulfone, polytetrafluoroethylene (PTFE), polyvinyl chloride (PVC) and polycarbonate. Each of these materials suffers from disadvantages. According to WO02/29397, PDMS and polyurethane are not injection mouldable, PVC is typically chemically impure, PMMA and polycarbonate are not particularly UV transparent (below 300 nm) and PTFE is typically not optically clear. Furthermore, polysulfone is very expensive both as a raw material and to process.

SUMMARY OF THE INVENTION

One of the objectives of the present invention is to provide a device for UV detection, suitable for use in systems for the separation and purification of chemicals, bio molecules or other components for use in pharmaceutical applications. Such systems should provide a sterilised environment in order to meet the strict requirements for such applications. Accordingly, it should be possible to sterilise the system by the use of gamma irradiation. Gamma irradiation is a preferred method for sterilising equipment prior to, for example, separation or purification of bio molecules. It will be understood that depending upon the dosage of gamma radiation used, microbial populations present in the equipment may not be eliminated totally but rather be significantly reduced in number. Unfortunately most polymers tend to block UV radiation after treatment with gamma irradiation. Furthermore, following gamma irradiation, UV radiation has a bleaching effect on most polymers, so that the UV absorption of the polymer is reduced the longer time the polymer is exposed to UV radiation. This effect results in an unstable signal for UV detection, which is a disadvantage.

Surprisingly, polypropylene has been found to be useful in a device for UV detection even after sterilisation with gamma irradiation. While following gamma irradiation the UV absorption of most polymers degrades over time as the polymers are irradiated with UV radiation, this was not found to be the case for polypropylene: the UV absorption of polypropylene was surprisingly found to remain very stable, even after extended periods (up to 40 hours) of UV irradiation (Table 1). Stability over time is important, as the typical run-time for a separation or purification experiment is relatively long (about 10 hours) and the application requirement is a maintained detector stability<10 mAU/h. As seen from Table 1, following gamma irradiation, polypropylene provides UV absorption stability significantly better than that. As seen from FIG. 1, polypropylene provides significantly improved UV absorption stability compared to PMMA. The total UV radiation intensity hitting the flow cell has been estimated to be approximately 3 μW in the experimental set-up used, with a spot size of approximately 5 mm$^2$ (Table 2), resulting in an estimated total UV radiation intensity hitting the flow cell of approximately 0.6 μW/mm$^2$.

Polypropylene has traditionally been rejected as a suitable material for UV detection because the UV transmission is only about 13% (±1%, λ=280 nm, measured for polypropylene, after gamma irradiation sterilisation, RF830MO, medical quality obtained from Borealis, Norway) for a 1 mm thick layer of material. However, it has been found that this transmission is sufficient when a UV light source of high intensity, like a Light emitting diode (LED), is used. LED's providing UV radiation are available from several suppliers, for example Sensor Electronic Technology Inc. (Columbia, S.C., USA). While most sources of UV radiation generate so much heat that they can easily cause polymers like thermoplastics to soften or melt, this is in general not the case for LED's. Polypropylene is injection mouldable and cheap both as raw material and to process. Furthermore, polypropylene is available in a quality fulfilling the requirements for USP class VI, which is a criteria to make it suitable for use in systems operating in highly regulated environments, such as, for example, systems for the separation, purification and preparation of chemicals, bio molecules, drugs or other components for use in medical or pharmaceutical applications.

Thus, in accordance with a first aspect of the present invention, there is provided a flow cell comprising a fluid inlet and a fluid outlet separated by a sample flow-through chamber comprising at least one UV-transparent window, characterised in that said at least one UV-transparent window is made of polymer material and has been subjected to Gamma radiation sterilisation. The word 'polymer' is herein defined to mean 'organic polymer'.

In one aspect, a dose of at least 10 kGy is used for the Gamma radiation sterilisation.

In another aspect, the polymer material has a UV-transmission in the range of between 1% and 40% per mm at a wavelength of 280 nm after being subjected to Gamma radiation sterilisation.

In a further aspect, the transmission of the polymer material after being subjected to Gamma radiation sterilisation does not vary by more than 10% during exposure for a period of 72 hours to UV-light of an intensity of approximately 0.6 μW/mm$^2$.

In another aspect, the transmission of the polymer material after being subjected to Gamma radiation sterilisation does not vary by more than 10% during exposure for a period of 48 hours to UV-light of an intensity of approximately 0.6 μW/mm$^2$.

In one aspect, the UV-transmission of the polymer material is greater than 2% and less than 30% per mm after being subjected to Gamma radiation sterilisation. Preferably, the UV-transmission of the polymer material is greater than 5% and less than 20% per mm after being subjected to Gamma radiation sterilisation. More preferably, the UV-transmission of the polymer material is greater than 12% and less than 18% per mm after being subjected to Gamma radiation sterilisation.

The flow cell of the present invention is easy to mount into the separation, purification or preparative system, as well as easy to dismount from the system, without the use of traditional coupling devices like screws, ferrules and sleeves. In the present invention this is achieved by the use of a specially constructed sealing means covering the main part of the device for UV detection. The sealing means is made from an opaque material in order to minimize the amount of stray light entering the detector, thus essentially no UV radiation, visible radiation or near infrared radiation can pass through the material. The sealing means may additionally comprise a UV radiation transmission window.

In one aspect, the flow cell is combustible. This is advantageous for a disposable system as it minimises the risk of chemical contamination and reduces environmental load.

According to a second aspect of the present invention there is provided a method for manufacturing a flow cell as herein before described, wherein the flow cell is made by moulding.

In a third aspect of the present invention there is provided a method for manufacturing a flow cell as herein before described, wherein the flow cell is made by injection moulding.

In accordance with a fourth aspect of the present invention there is provided a method for manufacturing a flow cell as herein before described, wherein the flow cell is made by extrusion.

In accordance with a fifth aspect of the present invention there is provided a method for manufacturing a flow cell as herein before described, wherein the flow cell is made by co-extrusion.

In accordance with a six aspect of the present invention there is provided a method for measuring UV absorption of a sample using a flow cell as herein before described. In one embodiment of the sixth aspect the UV radiation is provided by a Light emitting diode (LED).

According to a seventh aspect of the present invention, there is provided a kit of parts comprising a flow cell as herein before described and a UV absorption detector which is open on one side to facilitate changing the flow cell without loosening the tubes by simply attaching the unit from one side.

The skilled person will understand that in another aspect of the invention, there is provided a flow cell comprising a fluid inlet and a fluid outlet separated by a sample flow-through chamber comprising at least one UV-transparent window, characterised in that said at least one UV-transparent window is made of a polymer material that has a UV-transmission in the range of between 1% to 40% per mm at a wavelength of 280 nm after being subjected to Gamma radiation sterilisation. Preferably, the UV-transmission of the polymer material is greater than 2% and less than 30% per mm after being subjected to Gamma radiation sterilisation. More preferably, the UV-transmission of the polymer material is greater than 5% and less than 20% per mm after being subjected to Gamma radiation sterilisation. Most preferably, the UV-transmission of the polymer material is greater than 12% per mm and less than 18% per mm after being subjected to Gamma radiation sterilisation. Most preferably, the flow cell is combustible.

It will be understood by a person skilled in the art, that a cuvette comprising at least one UV-transparent window which is made of a polymer material and has been subjected to Gamma irradiation sterilisation is suitable for use in a method for measuring UV absorption of a sample. Preferably, the cuvette has been subjected to a dose of at least 10 kGy for Gamma radiation sterilisation. More preferably, the polymer material has a UV-transmission in the range of between 1% to 40% per mm at a wavelength of 280 nm after being subjected to Gamma radiation sterilisation. More preferably, the polymer material has a UV-transmission which is greater than 15% and less than 18% per mm after being subjected to Gamma radiation sterilisation. Most preferably, the cuvette is combustible.

BRIEF DESCRIPTION OF THE INVENTION

DETAILED DESCRIPTION OF THE INVENTION

Figure 1:
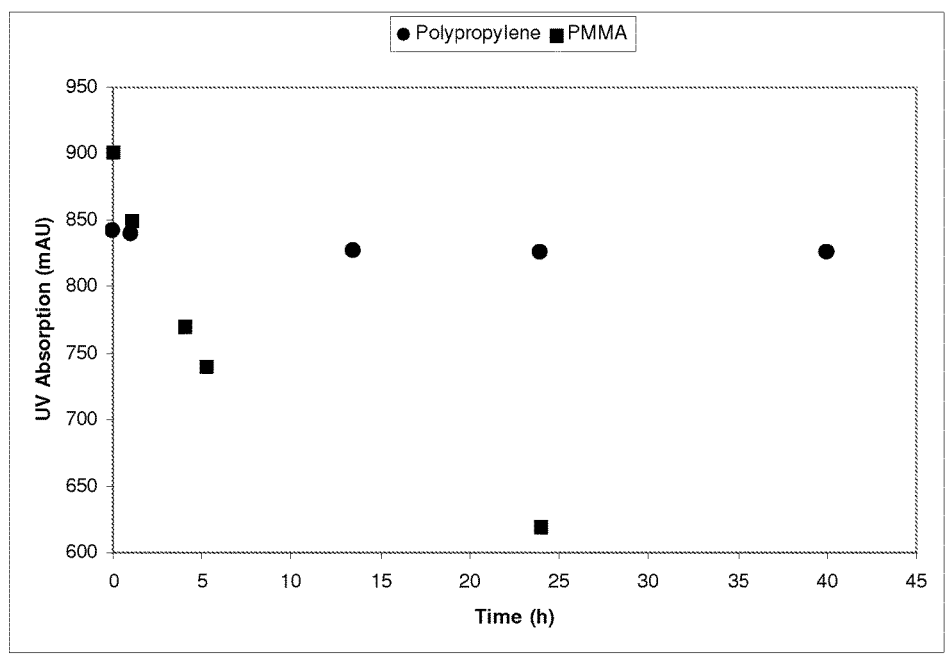
FIG. 1 is a graph demonstrating the UV absorption stability ($\lambda$=280 nm) of Polypropylene compared to PMMA.

A polymeric flow cell according to the present invention is typically positioned between a source of UV radiation and a detector for UV radiation.

The source of UV radiation can be a mercury (Hg) lamp, a Deuterium lamp, a Xenon lamp, a light emitting diode (LED), a hollow cathode lamp, a laser or any other source of UV radiation known by the person skilled in the art. The use of multiple radiation sources of the same sort, or combined use of different radiation sources is to be considered within the scope of the present invention. LED's may preferably be used, due to the low heat generation and stability of such radiation sources.

The detector for UV radiation can be a photomultiplier tube (PMT), a photodiode, a CCD camera or any other UV detector known by the person skilled in the art. It will be understood by a person skilled in the art that a spectrophotometer can also be used as a UV detector. The use of multiple detectors of the same sort, or combined use of different detectors (for example having different responses to radiation of different wavelengths, and/or having different dynamic ranges) is to be considered within the scope of the present invention. Typically, two detectors of the same type and performance are used: a sample detector to measure a sample signal, and a reference detector to measure a reference signal.

The radiation beam from the UV source is typically split into two separate beams by the use of a beamsplitter positioned between the UV source and the flow cell. The first beam proceeds from the beamsplitter through the flow cell to the sample detector. The second beam is typically reflected so that it travels to the reference detector, without passing through the flow cell.

Alternatively, both beams can be led to the same detector. In his case a chopper and some mirrors are used to alternately guide the light directly onto the detector or through the sample to the detector.

A flow cell according to the present invention can have an optical path length (indicated as H in FIG. 2) in the range 0.2-15 mm. Flow cells with different path lengths provide different dynamic ranges for the measurements. While a path length of 1 mm is suitable for an optically dense sample, a path length of 5 mm is suitable for samples having a lower optical density. While only one flow cell has been used in the figures to illustrate examples of different embodiments of flow cells according to the present invention, the use of two or more flow cells coupled in series is also conceivable. By coupling several flow cells having different optical path lengths in series, the dynamic range of the system is increased. Two or more flow cells according to the present invention can also be coupled in parallel. To minimize bandbroadening effects for flow cells coupled in parallel, a flow direction valve can be used to direct the sample flow sequentially to one flow cell at a time. Switching of the sample flow between the flow cells coupled in parallel can be performed at predetermined intervals. Alternatively the switching of the sample flow between the flow cells coupled in parallel can be performed in response to the signal obtained from the measurement of UV radiation.

FIG. 1 is a graph demonstrating the UV absorption stability of Polypropylene compared to PMMA. In one embodiment of the present invention, the flow cell is made of polypropylene.

Figure 2:
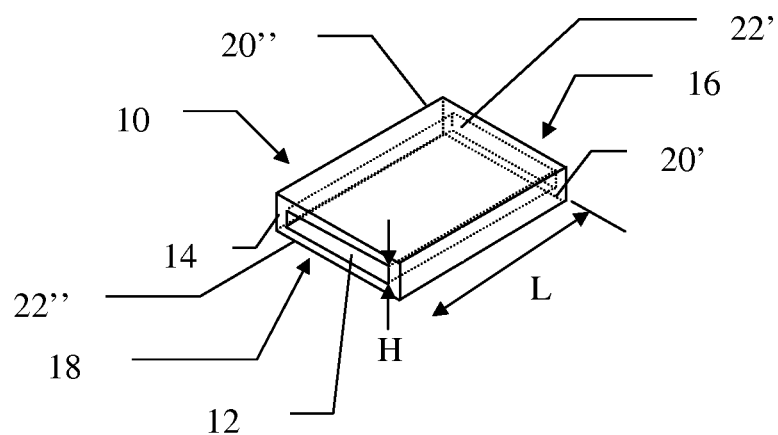
FIG. 2 is a schematic perspective view of a first embodiment of a flow cell according to the present invention.

FIG. 2 is a schematic perspective view of an embodiment of a flow cell (10) according to the present invention. Although illustrated here as being essentially quadratic the flow cell (10) can be of any geometrical shape. The flow cell is formed as a chamber (12) surrounded by a wall (14), an inlet (16) intended to receive a flow of liquid into the flow cell (10) and an outlet (18) intended to deliver a flow of liquid out from the flow cell (10). The flow cell (10) is shown as having a cross section formed as a rectangle with two short sides and two long sides, but other shapes such as square, oval, circular, etc are conceivable, with the chamber (12) defined by two pairs of interconnected walls—one pair of short walls (20', 20") and a pair of long walls (22', 22"). The two walls (20', 20", 22', 22") forming each pair of walls are typically parallel and aligned to each other. The two pairs of walls (20'-22") are positioned at an angle of 90 degrees to each other, forming the chamber (12) of the flow cell (10). The walls (22'-22") of the flow cell have a thickness<2 mm, preferably<15 mm, more preferably<1.0 mm, even more preferably<0.5 mm to facilitate transmission of UV radiation. During use UV light is intended to be transmitted from a source of UV-radiation (not shown) outside the flow cell through wall (22'), through chamber (12) and out through wall (22") to a detector of UV radiation. Walls (22', 22") thus act as windows into and out of the chamber (12). The distance (H) between the inner surfaces of wall 22' and 22" is preferably in the range 1-5 mm. As the walls, 22', 22" are essentially continuous in the embodiment shown, it can be understood that only one window is present for the entry and exit of UV Light into and from the chamber (12). It will further be understood that other embodiments are possible in which the flow cell has a circular or tubular configuration which would only require the presence of single, continuous window. A skilled person will also understand that n other embodiments a mirrored surface may be positioned opposite to a single window. The flow cell (10) has a cross sectional area less than 500 mm², preferably less than 50 mm² and a length (L) less than 100 mm, preferably less than 20 mm. With dimensions within these ranges, the backpressure of the flow cell is typically<0.5 Bar, operating at liquid flow rates between 25 ml/min and 9 L/min for aqueous solutions. When used in systems for chromatographic separation, operating at liquid flow rates between 25 ml/min and 9 L/min, the bandbroadening effect of a flow cell according to the present invention has been estimated to be less than 10%.

The flow cell (10) is preferably manufactured from a mouldable material. Further, the material of the flow cell (10) preferably fulfils the requirements for USP class VI materials. Even more preferably, the material of the flow cell (10) is a validated USP class VI material. The flow cell (10) according to the present invention can be manufactured by the use of moulding. Further, the flow cell (10) according to the present invention can be manufactured by the use of injection moulding. The flow cell (10) according to the present invention can also be manufactured by the use of extrusion. Further, the flow cell (10) according to the present invention can be manufactured by the use of co-extrusion. The flow cell (10) is preferably moulded in one single piece, but it is also possible to assemble the flow cell (10) from several parts. Table 3 lists the test results for a non-exhaustive list of examples of different materials that can be used for manufacturing a flow cell (10) according to the present invention.

Figure 3:
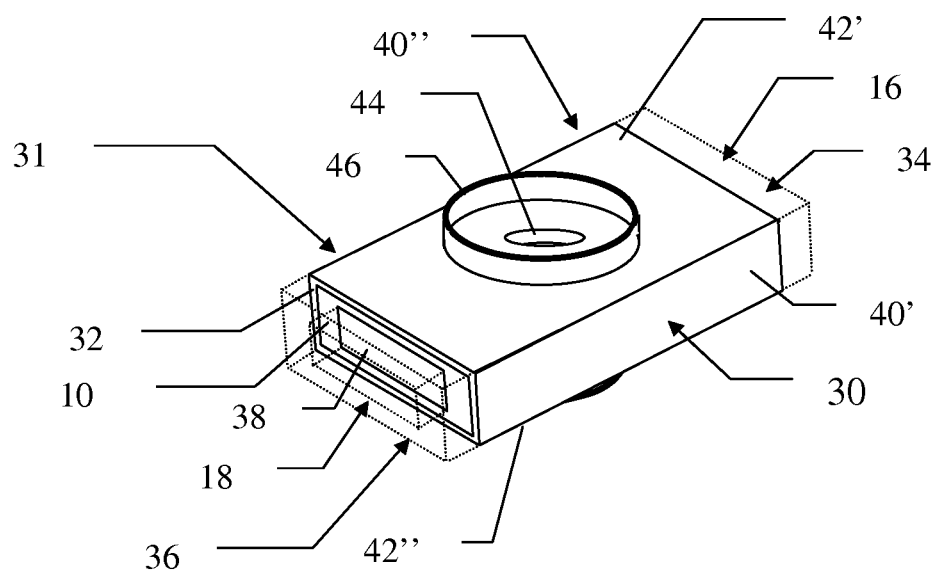
FIG. 3 is a schematic perspective view of a second embodiment of a flow cell according to the present invention.

FIG. 3 is a schematic perspective view of another embodiment of the invention. A specially designed sealing means (30) is fitted outside the flow cell (10) to provide a sealable flow cell (31). The single sealing means (30) provides sealing at both the inlet (16) and outlet (18) ends of the flow cell (10) and it also protects the potentially fragile flow cell (10) from breaking, if subjected to impacts or shocks during assembly or use. The sealing means (30) preferably covers all of the walls of the flow cell (10), except for at least one UV radiation transmission window (44). The sealing means (30) is preferably made of opaque material (in one embodiment SANTOPRENE™ TPV 181-64MED, Exxon Mobile Chemical, USA), so that essentially no UV radiation, visible radiation or near infrared radiation can pass through the material. Accordingly, the amount of stray light entering the flow cell and thus the detector is minimised.

The sealing means (30) is formed to fit outside the flow cell (10) described above. Accordingly, the sealing means (30) is typically formed as a housing defined by at least one wall (32), an inlet portion (34) intended to provide sealing around the inlet portion (16) of the flow cell (10) and an outlet portion (36) intended to provide sealing around the outlet portion (18) of the flow cell (10). The sealing means (30) is shown as having a cross section formed as a rectangle, but other cross-sectional shapes such as square, oval, circular, etc are conceivable, and encloses a chamber (38) defined by two pairs of walls (40', 40", 42', 42"). The chamber (38) is designed to tightly enclose a flow cell (10) and seal around it. The two walls (40', 40", 42', 42") forming each pair are typically parallel and aligned to each other. The two pairs of walls are positioned at an angle of 90 degrees to each other, forming the chamber (38) of the sealing means (30). One pair of the walls preferably has one UV radiation transmission window (44) on each wall. The two windows (44) are positioned opposite each other in alignment, so that beams of UV radiation can pass through both windows. The windows can be of any geometrical shape. The windows (44) are preferably formed as circles. The sealable flow cell (31) shown in FIG. 3 is shown having two UV radiation transmission windows (44), but the use of only one window (44) or more than two windows (44) is conceivable. Optionally, the sealing means comprises a raised rim (46) around the UV radiation transmission window (44), to provide a structure which facilitates sealing the optical path into and out from the flow cell (10). In the embodiment shown in solid lines, the end faces of the flow cell (10) are not covered by the sealing means which allows simplified manufacturing of the flow cell/sealing means assembly. However with this embodiment there is a risk of light entering the flow cell through the exposed end faces, and in a preferred embodiment of the invention, the exposed end faces of the flow cell (10) are also covered by the opaque sealing means as shown by dotted lines in FIG. 3.

The wall (40'-42") of the sealing means (30) preferably has a thickness<3 mm, preferably<1.5 mm, more preferably<1.0 mm, even more preferably<0.5 mm. The sealing means (30) is preferably resilient, to facilitate sealing against the flow cell and other components of the system to which it is intended to be used. The sealing means (30) is preferably manufactured from a mouldable material. Further, the material of the sealing means (30) preferably fulfils the requirements for USP class VI materials. Even more preferably, the material of the sealing means (30) is a validated USP class VI material. In one embodiment the flow cell (10) and the sealing means (30) are manufactured as separate parts, for example by the use of moulding. However, it is of course also possible to produce the flow cell (10) and the sealing means (30) as a single part, for example by the use of sequential moulding.

A sealable flow cell (31) according to the present invention can be manufactured by the use of moulding. Further, the sealable flow cell (31) according to the present invention can be manufactured by the use of injection moulding. The sealable flow cell (31) according to the present invention can also be manufactured by the use of extrusion. Further, the sealable flow cell (31) according to the present invention can be manufactured by the use of co-extrusion. The sealable flow cell (31) is preferably moulded in one single piece, but it is also possible to assemble the sealable flow cell (31) from several parts.

Figure 4:
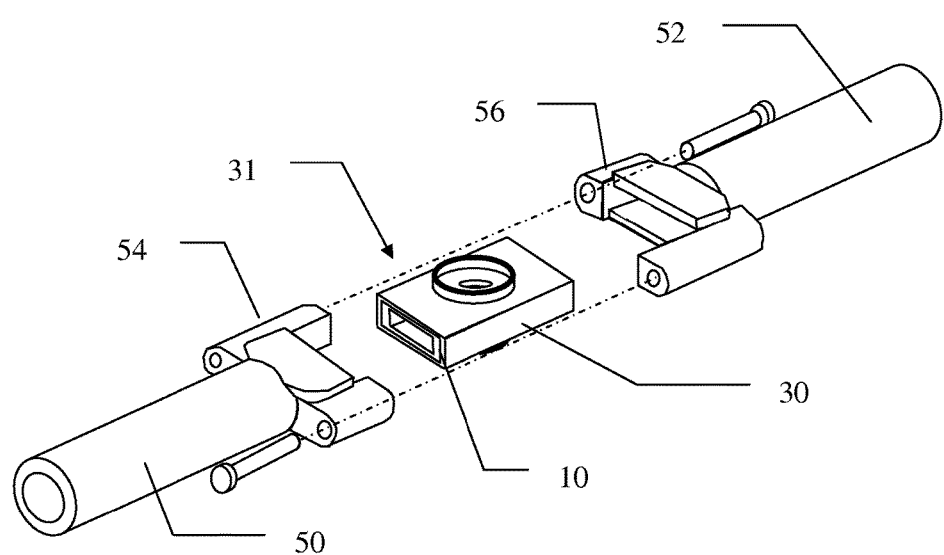
FIG. 4 is a schematic perspective exploded view demonstrating how an embodiment of a flow cell according to the present invention can be connected to liquid flow channels.

FIG. 4 is a schematic perspective exploded view demonstrating how an embodiment of a sealable flow cell (31) according to the invention, can be connected to liquid flow channels (50, 52). The sealable flow cell (31), comprising the flow cell (10) inside the sealing means (30), is easily inserted into the system to connect to the liquid flow channels (50, 52), without the use of regular sleeves and ferrules. The flow cell (10), inside the sealing means (30), can be connected by the use of holders (54, 56) to liquid flow channels (50, 52) as shown in FIG. 4. Of course it is also possible to mould the holders directly onto the sealing means (30) material fitted outside, or moulded directly onto, the flow cell (10).

The sealing means (30) enables the use of a UV detector that is open at one side. In the embodiment shown the flow cell can be exchanged without loosening of tubes by just sliding in the flow cell from the side. This is advantageous if the flow cell and the connecting liquid flow channel is sterilised as a whole.

A flow cell according to the present invention is suitable for use in a method for measuring UV absorption of a sample. Further, a flow cell according to the present invention is suitable for use in a method for measuring UV absorption of a sample in a chromatography system or in a filtration system. The source of UV radiation can be any source of UV radiation known by the man skilled in the art. In one method for measuring UV absorption of a sample the UV energy is provided by a LED.

TABLE 1

UV absorption (mAU, λ = 280 nm) of 1 mm polypropylene after sterilisation with gamma irradiation (20-30 kGy)

| Start | 1 h | 13.5 h | 24 h | 40 h |
|---|---|---|---|---|
| 842 mAU | 839 mAU | 827 mAU | 826 mAU | 826 mAU |

TABLE 2

Estimation of the total intensity of UV radiation (λ = 280 nm) hitting the flow cell, calculated from the equipment and the optical set-up used.

UV-LED intensity: 100 μW (+/−50 μW)
Transmission bandpass filter: 18% transmitted
Aperture: 2 mm diameter, original beam size 3 × 3 mm (rectangular shape): 35% transmitted
Reflection loss lens: 8% (92% transmitted)
Reflection loss beam splitter: 40% (+/−5%), 60% transmitted
Reflection loss window: 8% (92% transmitted)
Total intensity hitting flow cell: 3 μW, spot size approx. 5 mm$^2$

TABLE 3

UV transmission at 280 nm in materials after gamma-irradiation sterilisation.

| Manufacturer | Quality | Transmission sample at 280 nm before irradiation [%] | Transmission sample at 280 after irradiation with 25-30 Gy nm [%] | Sample thickness [μm] | Transmission at 280 nm after irradiation corrected for 1 mm thickness [%] |
|---|---|---|---|---|---|
| Honeywell (Fluoropolymers) | Aclar 11A | 90.2 | 87.2 | 102 | 26 |
| | Aclar 11C | 76 | 72 | 204 | 20 |
| | Aclar 22A | 91.6 | 89.7 | 60 | 16.5 |
| | Aclar 22C | 88.1 | 84.9 | 127 | 27.6 |
| | Aclar Ultrx3000 | 89.0 | 87.1 | 76.2 | 16.3 |
| Borealis | RF830P (USPVI) | 21.5 | 12.9 | 1000 | 12.9 |
| Polypropen (Polypropylenes) | HE820P | 6.68 | 4.7 | 1000 | 4.7 |
| Zeon Chemicals (Cyclo-olefin-polymers-COP) | Zeonex 480 (not USPVI) | 23.4 | 1.9 | 2000 | 13.9 |

The above examples illustrate specific aspects of the present invention and are not intended to limit the scope thereof in any respect and should not be so construed. Those skilled in the art having the benefit of the teachings of the present invention as set forth above, can effect numerous modifications thereto. These modifications are to be construed as being encompassed within the scope of the present invention as set forth in the appended claims.

What is claimed is:

1. A method for measuring UV absorption of a sample using a flow cell including a polypropylene material, the method comprising:
    subjecting the flow cell to a Gamma radiation sterilization procedure;
    conveying the sample through the flow cell;
    transmitting UV light through the polypropylene material and through the sample; and
    determining the UV absorption of the sample.

2. The method of claim 1, wherein the determining is based on the transmitted UV light.

3. The method of claim 2, wherein the determining includes measuring an intensity of the transmitted UV light.

4. The method of claim 3, wherein the measuring includes detecting the transmitted UV light using a detector disposed adjacent to the flow cell.

5. The method of claim 1, wherein the Gamma radiation sterilization procedure includes subjecting the flow cell to a dose of at least 10 kGy of Gamma radiation.

6. The method of claim 1, wherein the flow cell includes at least one of (i) a circular wall made of polypropylene and (ii) a polypropylene window.

7. The method of claim 1, wherein a UV transmission of the polypropylene material after being subjected to the Gamma radiation sterilization procedure does not vary by more than about 10% during an exposure to UV light for a period of about 72 hours.

8. The method of claim 7, wherein an optical power density during the exposure to UV light is about 0.6 μW/mm$^2$.

9. The method of claim 1, wherein a UV transmission of the polypropylene material after being subjected to the Gamma radiation sterilization procedure does not vary by more than about 10% during an exposure to UV light for a period of about 48 hours.

10. The method of claim 9, wherein an optical power density during the exposure to UV light is about 0.6 μW/mm$^2$.

11. The method of claim 1, wherein the polypropylene material has a UV transmission in the range of between 1% and 40% per mm at a wavelength of 280 nm after being subjected to the Gamma radiation sterilization procedure.

12. The method of claim 1, wherein a UV-transmission of the polypropylene material is greater than 2% and less than 30% per mm after being subjected to the Gamma radiation sterilization procedure.

13. The method of claim 1, wherein a UV-transmission of the polypropylene material is greater than 5% and less than 20% per mm after being subjected to the Gamma radiation sterilization procedure.

14. The method of claim 1, wherein a UV-transmission of the polypropylene material is greater than 12% and less than 18% per mm after being subjected to the Gamma radiation sterilization procedure.

15. The method of claim 1, wherein the conveying includes delivering the sample to the flow cell in one of a chromatography system and a filtration system.

16. The method of claim 1, further comprising sealing the flow cell utilizing a sealing means.

17. The method of claim 1, wherein the conveying includes flowing the sample in at least one channel of the flow cell.

18. A flow cell for measuring UV absorption of a sample, the flow cell comprising:
   polypropylene windows having been subjected to a Gamma sterilization procedure; and
   a sealing means configured to provide an interface between the flow cell and (i) a fluidic port of one of a filtration and a chromatography system and (ii) a UV absorption detector module.

19. The flow cell of claim 18, wherein the flow cell is combustible.

20. The flow cell of claim 18, further comprising a chamber formed between the polypropylene windows, the chamber being configured to house the sample.

\* \* \* \* \*